| United States Patent [19] | [11] Patent Number: 4,812,597 |
| Imai et al. | [45] Date of Patent: Mar. 14, 1989 |

[54] DEHYDROGENATION OF DEHYDROGENATABLE HYDROCARBONS

[75] Inventors: Tamotsu Imai, Mount Prospect; Jeffery C. Bricker, Buffalo Grove, both of Ill.

[73] Assignee: UOP Inc., Des Plaines, Ill.

[21] Appl. No.: 92,355

[22] Filed: Sep. 2, 1987

[51] Int. Cl.$^4$ .............................................. C07C 5/48
[52] U.S. Cl. .................................. 585/443; 585/444; 585/445; 585/627; 585/629
[58] Field of Search ............ 585/443, 444, 445, 627, 585/629

[56] References Cited

U.S. PATENT DOCUMENTS

| | | | |
|---|---|---|---|
| 3,380,931 | 4/1968 | Ryland | 252/432 |
| 3,437,703 | 4/1969 | Reitmeier et al. | 260/669 |
| 3,670,044 | 6/1972 | Drehman et al. | 260/683.3 |
| 3,855,330 | 12/1974 | Mendelsohn et al. | 260/669 R |
| 4,113,656 | 9/1978 | Riley et al. | 252/439 |
| 4,376,724 | 3/1983 | Mita et al. | 252/460 |
| 4,435,607 | 3/1984 | Imai | 585/443 |
| 4,435,607 | 3/1984 | Imai | 585/443 |
| 4,565,898 | 1/1986 | O'Hara et al. | 585/445 |
| 4,652,687 | 3/1987 | Imai et al. | 585/445 |
| 4,691,071 | 9/1987 | Bricker | 585/444 |
| 4,717,779 | 1/1988 | Bricker et al. | 585/444 |

*Primary Examiner*—Asok Pal
*Attorney, Agent, or Firm*—Thomas K. McBride; Raymond H. Nelson

[57] ABSTRACT

Dehydrogenatable hydrocarbons may be subjected to a dehydrogenation reaction in which the hydrocarbons such as ethylbenzene are treated with a dehydrogenation catalyst comprising a modified iron catalyst in the presence of steam. The reaction mixture containing unconverted ethylbenzene, styrene, hydrogen and steam is then contacted with an oxidation catalyst in a second zone whereby hydrogen is selectively oxidized to the substantial exclusion of oxidation of the hydrocarbon. The selective oxidation catalyst which is employed will comprise a noble metal of Group VIII of the Periodic Table, a metal of Group IVA and, if so desired, a metal of Group IA or IIA composited on a porous inorganic support such as alumina. The noble metal of Group VIII of the Periodic Table will be present in the exterior surface of the support which possesses a depth in the range of from about 10 to about 300 microns in an average concentration at least 10% than the Group VIII noble metal average concentration in the core of the support.

17 Claims, No Drawings

DEHYDROGENATION OF DEHYDROGENATABLE HYDROCARBONS

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reaction continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and high styrene selectivity are achievable.

The combustion of hydrogen with the oxygen in the oxygen-containing gas requires the presence of an oxidation catalyst. There are some key requirements for the oxidation catalyst to be usable for such a purpose. The most important catalytic property required is good catalytic stability since the oxidation catalyst must survive under very severe reaction conditions, namely at about 600° to 650° C. in the presence of steam. Under such conditions, porous inorganic materials such as aluminas, silicas and zeolites cannot maintain their pore structures for a long prriod of time, resulting in the permanent damage of catalysts prepared using such materials as supports, e.g., platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide, graphite with a major portion of a phosphate species. In addition to these dehydrogenation catalysts, the reaction also employs a catalyst for the oxidation step of the process comprising platinum or palladium in elemental form or as a soluble salt. Another U.S. Pat. No. 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxddation catalyst while introdccing oxygen into the reaction medium. The dehydrogeaation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular sieves zeolite-type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a concomitantly lower selectivity to carbon monoxide and carbon dioxide. In addition, the patentee teaches the use of one catalyst for both dehydrogenation and oxidation which is in contrast to the separate dehydrogenation and oxidation catalysts which are used in the present process.

In addition to the aforementioned U.S. patents, U.S. Pat. No. 4,435,607 also discloses a method for the dehydrogenation of dehydrogenatable hydrocarbons utilizing a two-step process which includes dehydrogenation followed by a selective oxidation process. The catalyst which is employed for the selective oxidation will comprise a noble metal of Group VIII, a metal of Group IVA and, if so desired, a metal of Group IA or IIA of the Periodic Table composited on a highly porous inorganic support.

Other U.S. patents which pertain to catalytic compositions of matter include U.S. Pat. No. 4,113,656 which describes a process for achieving the distribution of metals on a support which requires quite small particles of the carrier as a nucleating agent for the catalytic metal deposited thereon. In addition, U.S. Pat. No. 4,376,724 discloses the dispersion of rhodium on a silica or titania support in which the metal is dispersed on the support in what is referred to as an eggshell distribution.

As will hereinafter be shown in greater detail it has now been discovered that by dispersing the active catalytic components on a support in a certain manner it is possible to obtain a superior catalyst with relation to stability and conversion of hydrocarbons to desired products over those catalysts which have been used in prior processes.

BRIEF SUMMARY OF THE INVENTION

This invention relates to a process for the dehydrogenation of dehydrogenatable hydrocarbons. More specifically, the invention is concerned with a process for the dehydrogenation of a dehydrogenatable hydrocarbon in which the hydrocarbon which is to undergo treatment is subjected to a dehydrogenation step in the presence of a dehydrogenation catalyst. This dehydrogenation step is followed by a selective oxidation step in which the product mixture which results from the aforementioned dehydrogenation step is treated in the presence of certain catalytic compositions of matter which are hereinafter set forth in greater detail in such a manner whereby the hydrogen which is present and which has resulted from the dehydrogenation step is selectively oxidized with a concomitant minimum oxidation of the hydrocarbons. By utilizing the particular selective oxidation catalyst, it is possible to obtain the desired dehydrogenated hydrocarbons in a relatively high yield as well as maintaining the stability and activity of the catalyst to a greater degree than has heretofore been experienced. By maintaining the aforementioned stability and activity, it is possible to obviate the necessity for relatively frequent changes of the catalyst or, in the alternative, regenerating the catalyst, thereby adding to the commercial attractiveness and economical feasibility of the dehydrogenation process.

It is therefore an object of this invention to provide a process for the dehydrogenation of dehydrogenatable hydrocarbons.

A further object of this invention is to provide a catalyst for the selective oxidation step of the process whereby hydrogen which is formed during the dehydrogenation process will be selectively oxidized to the substantial exclusion of the oxidation of the hydrocarbons.

In one aspect an embodiment of this invention resides in a process for the dehydrogenation of a dehydrogenatable hydrocarbon with separate and intermediate selective oxidation of hydrogen which comprises the steps of:

(a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of dehydrogenated hydrocarbons, unconverted hydrocarbons, hydrogen and steam;

(b) removing said first-reaction dehydrogenation zone effluent stream from said first-reaction dehydrogenation zone;

(c) passing said effluent stream of step (b) to a second-reaction oxidation zone which is separate and discrete from said first-reaction dehydrogenation zone;

(d) contacting said first reaction dehydrogenation zone effluent in said second-reaction oxidation zone with an oxygen-containing gas in the presence of an oxidation catalyst consisting essentially of a Group VIII noble metal, a Group IVA metal and a group IA or IIA mttal composited on an alumina support at oxidation conditions to selectively oxidize said hydrogen within said first-reaction zone effluent to the substantial exclusion of oxidation of said unconverted and dehydrogenated hydrocarbons, wherein said exothermic selective oxidation of said hydrogen provides additional heat and thereby raises the temperature of said unconverted and dehydrogenated hydrocarbons;

(e) withdrawing said unconverted and dehydrogenated hydrocarbons from said second-reaction oxidation zone having an increased temperature with respect to the temperature of said first-reaction dehydrogenation zone effluent;

(f) passing said second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and, (g) withdrawing and recovering said dehydrogenated hydrocarbons, the improvement of which comprises utilizing as said oxidation catalyst an alumina support onto which the Group VIII noble metal has been surface impregnated.

A specific embodiment of this invention is found in a process for the dehydrogenation of ethylbenzene which comprises contacting said ethylbenzene with a dehydrogenation catalyst comprising an alkaline metal modified iron catalyst at a temperature in the range of from about 500° C. to about 700° C. and a pressure in the range of from about 0.1 to about 10 atmospheres in the presence of steam, thereafter contacting the resultant mixture of unconverted ethylbenzene, styrene, hydrogen and steam with air at a temperature in the range of from about 500° to about 700° C. and a pressure in the range of from about 0.1 to about 10 atmospheres in the presence of a catalyst comprising a mixture of platinum, tin and lithium composited on an alumina support, said catalyst being characterized in that the platinum is present on the exterior surface which possesses a depth in the range of from about 10 to about 300 microns of said alumina support in an average concentration which is at least 10% higher than the average concentration of platinum which is present in the core of said support whereby hydrogen is selectively oxidized, and recovering the desired styrene after the final stage of dehydrogenation.

Other objects and embodiments will be found in the following detailed description of the invention.

DETAILED DESCRIPTION OF THE INVENTION

As hereinbefore set forth, the present invention is concerned with a dehydrogenation process for the dehydrogenation of dehydrogenatable hydrocarbons which involves the use, in one step of the process, of a selective oxidation catalyst which will provide improved stability and effectiveness of the active elements as well as eliminating some disadvantages which have been present with prior catalytic compositions of matter used in the same process.

As was previously discussed, catalysts have been disclosed as containing a Group VIII metal supported on alumina in the presence of modifying compounds or metals such as Group IVA elements. The stability, activity and selectivity of such catalysts are often limited by pore diffusion. In addition, the particle size of the catalysts is also an important factor. For catalyst particles wiich are physically large in size the effectiveness factor which may be defined as the Active Metal Site divided by the Total Metal Site is decreased significantly. The importance of the particle size is due to the necessity for achieving a low pressure drop, this being especially true for dehydrogenation reactions wherein a pressure increase will decrease the level of equilibrium conversion. Therefore, in any dehydrogenation reactions the conversion of the dehydrogenatable hydrocarbon is relatively sensitive to the pressures which are employed to effect the conversion. For example, in the conversion of ethylbenzene to styrene, as the pressure which is employed increases, the equilibrium conversion level decreases in a significant manner. As will hereinafter be shown in greater detail we have now discovered that by preparing the selective oxidation catalyst in a particular manner it is possible to obtain a catalyst which comprises particles of relatively large size which possess a relatively high effectiveness factor.

In the present process, a dehydrogenatable hydrocarbon of the type hereinafter set forth in greater detail is contacted with a dehydrogenation catalyst in the presence of steam in a multicatalyst bed system. Inasmuch as the dehydrogenation of the hydrocarbon is endothermic in nature, it is necessary to provide an additional amount of heat before the product enters the next catalyst bed in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen with the resultant composition thereof is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidation catalyst, both of the type hereinafter set forth in greater detail, are loaded in the apparatus in alternate layers. The number of alternate layers of dehydrogenation catalyst and selective oxidation catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which include lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassuum hydroxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition to these catalysts, other well-known dehydrogenation catalysts which may be utilized will include those comprising ferric oxide, potassium oxide, as well as other metal oxides and/or sulfides of metals of Groups IA, IIA, IVB, VB and VIB of the Periodic Table including those of calcium, lithium, strontium, magnesium, beryllium, zirconium, tungsten, molybdenum, hafnium, vanadium, copper, chromium and mixtures of two or more oxides such as chromia-alumina, chromia-titania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C.and at a reaction pressure in the range of from about 0.1 to about 10 atmospheres; the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention. After contacting the dehydrogenation catalyst with the steam and hydrocarbon, the resulting mixture comprising unconverted hydrocarbon, dehydrogenated hydrocarbon, steam and hydrogen which has passed through the catalyst bed is contacted in a separate zone with the selective oxidative catalytic composition of the type hereinafter set forth in greater detail. In addition, oxygen-containing gas is introduced into the reactor, preferably at a point adjacent to the oxidation catalyst bed. Examples of oxygen-containing gases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidation catalyst whereby hydrogen is selectively oxidized to water with a minimal amount of reaction of oxygen with the hydrocarbons, either unconverted hydrocarbon or dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenatable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnapthalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as ethylene, propylene, 1-butene, 2-butene, 1-pentene, 2-pentene, 1-hexene, 2-hexene, 3-hexene, and branched chain derivatives thereof, etc.

The selective oxidation step of the process utilizes, as hereinbefore set forth, the hydrogen which has been produced in the dehydrogenation step of the process to supply heat to the inlet of the next dehydrogenation catalyst bed. Inasmuch as temperatures which are utilized in the process may be as high as 650° C. in the presence of steam, the operating conditions in which the oxidation catalyst must function are severe in nature. In order for the oxidation catalyst to remain stable and minimize the carbon formation thereon, the catalyst support must be calcined at a relatively high temperature in order to decrease the surface area, this decrease in surface area contributing to the stability of the catalyst. Conventional oxidation catalysts utilizing a porous support such as alumina which had been calcined at relatively low temperatures, i.e., below about 900° C. or lower, lose surface area at a rapid rate and form excessive carbon on the surface thereof, thus resulting in a deactivation of the catalyst.

An effective oxidation catalyst which may be used in the dehydrogenation and selective oxidation process of the present invention comprises a noble metal of Group VIII of the Periodic Table such as platinum along with a Group IVA metal of the Periodic Table such as tin and, if so desired, a metal selected foom Group IA and IIA of the Periodic Table composited on a solid porous inorganic oxide support. This type of inorganic oxide support is not critical to this invention, however, a particularly effective support which contributes to the stability and effectiveness of the catalyst comprises an alumina. The alumina support will be derived from various types of aluminas such as, for example, boehmite, pseudoboehmite, gibbsite, etc., or a precursor of an alumina such as an aluminum hydroxyl chloride sol. The calcination of the support is effected at a temperature within the range of from about 600° to about 1500° C. prior to impregnation of the metals thereon. If so desired, the calcination of this support may be effected in a dry atmosphere, preferably at a temperature in the range of from about 800° to about 1500° C.or the calcination may be effected in a hydrous atmosphere such as that provided by steam, the temperatures preferably in the range of from about 600° to about 1300° C. The calcination of the support within these temperature ranges will be effected over a period of time which may range from about 0.5 to about 30 hours or more in duration and it is to be understood that the particular temperature which is selected for the calcination of the support will influence or direct the time frame during which the calcination takes place. It has been found that a particularly effective type of alumina source which may be in the form of pellets, spheres, powder, slurry, etc. and which will provide desired catalyst support. In addition, the alumina may be present as alpha-alumina or as a mixture of alpha-alumina and thetaalumina.

As was hereinbefore set forth, the selective oxidation catalysts which are employed in the process of this invention will comprise a noble metal of Group VIII of the Periodic Table and a metal of Group IVA of the Periodic Table composited on a solid inorganic support which, prior to the compositing of the metals thereon, has been calcined at a temperature within the range herebefore discussed. In addition, if so desired, it is also contemplated within the scope of this invention that the catalyst will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight. Of the metals of Group IVA of the Periodic Table, germanium, tin and lead comprise the preferred species, these metass also being present in the final catalyst composite in an amount in the range of from about 0.005% to about 5% by weight. The preferred species of metals of Group IA or IIA of the Periodic Table will include lithium, sodium, potassium, rubidium, cesium, beryllium, magnesium, calcium, barium, francium, and radium, the alkali metals or alkaline earth metals being present in an amount in the range of from about 0.005% to about 5% by weight of the catalyst composite.

The catalytic metal portion of the finished catalyst is impregnated on the surface of the catalyst support in such a manner so that the finished composite will contain the Group VIII noble metal on the exterior surface of the support in at least a 10% higher average concentration than the Group VIII noble metal average concentration which is present in the core of the support. For purposes of this invention the term "exterior surface" as used in the present specification and dependant claims will refer to that portion of the catalyst particle which extends from the surface of the particle to a depth which is in a range of from about 10 to about 300 microns. In addition, the term "average concentration" as herein used will be defined as the weight of the noble metal in a given region of the particle divided by the total weight of the region. By utilizing the surface impregnation technique of the present invention it is possible to obtain an improved catalyst which contains at least a 10% higher Group VIII noble metal average concentration on the exterior surface, as previously defined, of the support as compared to the average concentration of Group VIII noble metal in the core of the particle. The higher Group VIII noble metal average concentration in the exterior surface will result in a greater overall effectiveness factor for the finished catalyst composite.

The desired surface impregnation of the catalyst may be effected in any suitable manner. In one method of preparation the Group VIII noble metal and the Group IVA metal may be coimpregnated through formation of a complex in the impregnation solution. The formation of this complex constitutes a significant factor inasmuch as the complex formed between the two metals is bulky in nature and its adsorption properties are such that it is deposited on the exterior surface of the catalyst particle during the impregnation step thereby insuring the deposition of a higher average concentration of Group VIII metal in the aforesaid exterior surface. In one embodiment of the invention the formation of the complex is accomplished by utilizing tin of the type hereinbefore set forth in greater detail in a +2 form. Alternatively, if tin is in a +4 form or other Group IVA metals are used a complex may be effected by utilizing, in the impregnation solution, a compound which possesses both a functional group as exemplified by a thio, amino, hydroxyl, or phosphorous moiety as well as a polar group such as a carboxyl or hydroxyl moiety in the compound. Examples of these compounds will include thiomalic acid, thiolactic acid, ethylenediaminetetraacetic acid, thioglycolic acid, thiopropionic acid, thiodiacetic acid, thiodipropionic acid, etc. It is to be understood that these compounds are only representative of the type of complexing compounds which may be employed, and that the present invention is not necessarily limited thereto.

Another alternative method of preparing the desired selective oxidation catalyst of the present invention is to impregnate the alumina support with a Group IVA metal which may be in the form of beads, spheres, pellets, etc. with an aqueous solution of the metal of Group IVA of the Periodic Table in which a soluble salt such as tin chloride, tin bromide, tin sulfate, lead chloride, lead persulfate, germanium chloride, etc. is present in the solution in an amount sufficent so that the finished catalytic composite will contain the desired amount of the metal. The impregnation is allowed to proceed for a predetermined period of time following which the composite is recovered, dried and calcined. Alternatively, the Group IVA metal may be incorporated into the alumina during the alumina forming step, by employing a suitable Group IVA containinng compound. In this case, the Group IVA compound may be added toaan alumina sol or alumina dough which may be oil-dropped or extruded to form the desired alumina composite. The composite is dried and calcined to form the final support containing Group IVA metal. Thereafter the Group IVA metal containing alumina support is then surface-impregnated with an aqueous solution of a noble metal of Group VIII of the Periodic Table and, if so desired, a polar compound which assists in the surface-impregnation of the Group VIII noble metal along with a metal of Group IA or IIA of the Periodic Table, both metals being present in an amount sufficient to provide the desired amount of the metals in the finished catalytic composite. For example, it is possible to employ a soluble salt of a noble metal of Group VIII of the Periodic Table such as chloroplatinic acid, chloropalladic acid, rhodium chloride, platinum sulfate, palladium sulfate, etc. and soluble salts of a metal of Group IA or IIA such as potassium chloride, potassium bromide, potassium iodide, sodium chloride, sodium bromide, rubidium chloride, rubidium bromide, rubidium nitrate, rubidium acetate, cesium chloride, cesium bromide, cesium nitrate, cesium acetate, calcium chloride, barium chloride, barium bromide, barium propionate, lithium chloride, lithium bromide, lithium dithionate, lithium nitrate, lithium iodide, lithium sulfide, etc. After allowing the impregnation to proceed for a period of time sufficient to permit the deposition of the desired amount of metal on the catalyst support, the composite is recovered, dried and calcined at a temperature in the range of from about 500° to about 600° C. or more in an air or air-steam atmosphere and recovered.

By utilizing this surface impregnation technique in which complex of the noble metals of Group VIII of the Periodic Table and metals of Group IVA of the Periodic Table are complexed, a higher average concentration of the Group VIII noble metal will be positioned in the exterior surface of the support relative to the core and thus will raise the effectiveness of the metal to function as a selective oxidation for the hydrogen present in the dehydrogenation zone effluent. In addition, by effecting the deposition of the noble metal of Group VIII of the Periodic Table on the exterior surface it will be possible to utilize a lesser amount of the costly metal, and thus lower the overall cost of the finished catalyst composite.

Some specific examples of selective oxiation catalytic compositions of matter which may be used in the process of the present invention comprise, as hereinbefore set forth, the noble metals of Group VIII; a metal of Group IA or IIA, a metal of Group IVA, composited on a theta or alpha-alumina which has been calcined at a temperature within the ranges hereinbefore set forth. These examples will include platinum, germanium and lithium composited on alumina, palladium, germanium and potassium composited on alumina, rhodium, germanium and potassium composited on alumina, platinum, tin and potassium composited on alumina, palladium, tin and potassium composited on alumina, rhodium, tin and potassium composited on alumina, platinum, germanium and cesium composited on alumina, palladium, germanium and cesium composited on alumina, rhodium, germanium and cesium composited on alumina, platinum, tin and cesium composited on alumina, palladium, tin and cesium composited on alumina, rhodium, tin and cesium composited on alumina, platinum, germanium and barium composited on alumina, palladium, germanium and barium composited on alumina, rhodium, germanium and barium, alumina, palladium, tin and barium composited on alumina, rhodium, tin and barium composited on alumina, platinum, lead and potassium composited on alumina, palladium, lead and potassium composited on alumina, rhodium, lead and potassium composited on alumina, etc. It is to be understood that the above-enumerated catalysts are only representative of the selective oxidation composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated.

By utilizing the catalyst which has been prepared by surface impregnating the catalytic metals, it is possible to obtain a catalyst system which exhibits the desired characteristics of stability and activity which is in contradistinction to oxidation catalysts which have been set forth in the prior art, the latter being unable to produce the desired stability which is exhibited by the catalyst of the present invention, and therefore cannot survive in use for a relatively long period of time. This relatively short life of a catalyst discourages the commercial use of such catalysts as unattractive due to the necessity of having to replace or regenerate the catalyst after a short interval of operating time has elapsed. In addition, the catalysts of the present invention also exhibit a definite activity for the selective oxidation of hydrogen rather than a tendency for the oxidation of the dehydrogenated products or unreacted hydrocarbons.

The catalyst of the present invention will exhibit an excellent stability in that it possesses the ability to maintain the maximum temperature of the reaction at a position which is near the inlet of the catalyst bed. The desired reaction, that is, the selective oxidation of hydrogen, is highly exothermic in nature and it is therefore an indication of a good catalyst that the maximum temperature is maintained near the inlet of the catalyst bed, thus indicating that the conversion of the hydrogen occurs at a time shortly after the product stream comprising unconverted hydrocarbons, dehydrogenated hydrocarbons, steam and hydrogen enters the catalyst bed. In addition, as will hereinafter be demonstrated, the catalyst of the present invention also possesses the ability to effect a relatively high conversion of oxygen as is evidenced by the absence of oxygen in the exit gas which is withdrawn from the reaction zone containing the selective oxidation catalyst.

The following examples are given for purposes of illustrating the selective oxidation catalyst of the present invention as well as to a process utilizing the selective oxidation catalyst in said process. However, it is to be understood that these examples are merely illustrative in nature and that the present process is not necessarily limited thereto.

EXAMPLE I

A selective oxidation catalyst in which the catalytic metals were uniformly distributed through the support were charged by adding a Boehmite powder to a mixer along with nitric acid, following which the mixer was capped and stirred. The resultant dough, after stirring for a period of about 8 minutes, was passed to an extruder and extruded through a dieplate. The extrudate product was dried for a period of 3 hours at 150° C. in a forced air draft oven and thereafter calcined. The calcination was effected at a temperature of 1330° C. for a period of 3 hours and thereafter slowly cooled.

The impregnation of the extrudates which measured 3.5 mm by 6 mm was effected by charging a chloroplatinic acid solution into a flask to afford 0.4 weight percent platinum based on the weight of the calcined support, followed by charging a lithium nitrate solution in an amount sufficient to afford 0.2 weight percent lithium based on the weight of the calcined support. Following this nitric acid was charged to the flask along with deionized water to afford an impregnated solution/calcined support ratio of 1/1 (vol/vol). As the last component of the impregnating solution, a sufficient amount of tin tetrachloride pentahydrate was added to affod 0.18 weight percent of tin based on the calcined support. The impregnating solution was added to a glass jacketed rotary evaporator followed by addition of the calcined support extrudates. A nitrogen purge was initiated at a rate of 1,000 cc/min. and the rotary evaporator was cold rolled for a period of 15 minutes. Following this, steam was charged to the evaporator jacket and evaporated until the presence of moisture was not detected at the mouth of the evaporator. The impregnated extrudate was then dried in a forced draft oven at a temperature of 150° C. for a period of 2 hours and thereafter the dried catalyst was ooaded into a quartz tube. The impregnated support was then calcined in a stream of air at a rate of 0.5 liters/min. while the temperature was raised from ambient to 650° C. during a 2 hour period. Upon reaching this temperature, air which had been passed through water heated to a temperature of 65° C. was passed through the quartz tube while maintaining the temperature of 650° C. for a period of 2 hours. At the end of this time the temperature was maintained for an additional period of 1 hour in a flowing dry air stream and thereafter the catalyst was cooled to ambient temperature in flowing air.

EXAMPLE II

In this example a surface impregnated selective oxidation catalyst of the present invention was prepared by mixing Boehmite powder with nitric acid in a mixer for a period of 8 minutes, drying and calcining in a manner similar to that set forth in Example I above.

The calcined extrudate was surface impregnated by treating the calcined support with an impregnating solution comprising chloroplatinic acid in which there was 0.4 weight percent platinum based on the weight of said calcined support, lithium nitrate which contained 0.2 weight percent lithium based on the weight of the calcined support, tin dichloride dihydrate in an amount sufficient to afford 0.5 weight percent tin based on the weight of the calcined support, nitric acid in a quanity equal to 16.4 weight percent based on the weight of the calcined support and a sufficient amount of deionized water to afford an impregnating solution/calcined support ratio of 1/1 (vol/vol). The calcined support and impregnating solution were placed in a glass jacketed rotary evaporator, purged with nitrogen and cold rolled for a period of 15 minutes. Upon completion of the cold rolling, steam was charged to the evaporator jacket and the impregnating solution was evaporated until the presence of moisture was not detectable at the mouth of the evaporator.

The impregnated support was then dried in a forced draft oven at a temperature of 150° C. for a period of 2 hours and thereafter calcined in a manner similar to that set forth in Example I above. The calcined catalyst system was then recovered. Analysis of the metal loadings of the catalyst prepared according to Example I which is labeled Catalyst A, and a catalyst prepared according to the method set forth in this example which is labeled Catalyst B are set forth in the table below.

TABLE 1

| | Metal Loadings | | | |
|---|---|---|---|---|
| | Pt, wt % | Sn, wt % | Li, wt % | $H_2$/Pt |
| Catalyst A | 0.4 | 0.2 | 0.19 | 0.47 |
| Catalyst B | 0.4 | 0.3 | 0.19 | 0.03 |

It is apparent from the above table that the catalyst prepared according to the process of the present invention, that is Catalyst B, possesses a lower hydrogen/platinum dispersion which is indicative of a more severe surface concentration or higher average concentration of the platinum on the surface as compared to Catalyst A.

EXAMPLE III

The catalysts which were prepared according to the above example were evaluated for various characteristics. The catalysts in an amount of 50 cc were loaded into a ⅞" inner diameter stainless steel reactor having a 100" long ½" diameter bore for the catalyst loading. The reactor was heated to an inlet temperature of 570° C. and a feedstock comprising a mixture of ethylbenzene, styrene, steam, hydrogen, oxygen and nitrogen which simulated a product stream at about a 60% ethylbenzene conversion from the second dehydrogenation catalyst bed of a three dehydrogenation catalyst bed reactor system having an oxidation catalyst bed positioned between the dehydrogenation catalyst beds was fed to the reactor. The feedstream was passed over the oxidation catalyst bed at the aforesaid inlet temperature and at a reactor outlet pressure of 0.7 atmospheres. The hydrocarbon feed was maintained at a Liquid Hourly Space Velocity of 10.3 hours$^{-1}$. The inlet feed ratio of the feed stream of ethylbenzene and styrene/$H_2O$/$H_2$/$O_2$/$N_2$ was 1.0/9/0.45/0.13/1. In addition, the air into the catalyst bed was controlled in order to maintain a maximum temperature of 630° C. in the reactor.

As an indication of the stability of the catalyst, measurements were taken to determine the position of the maximum temperature which was present in the bed of catalyst. As was previously set forth, the maximum catalyst temperature should be at a location near the inlet position of the catalyst. The desired reaction, which is the selective oxidation of hydrogen, is highly exothermic in nature and one feature which determines the stability and effectiveness of a catalyst composite is the stability of the position at which maximum catalyst temperature is maintained in the catalyst bed. In addition, another indication of catalyst performance resides in the styrene combustion selectivity and in the amount of air necessary to achieve the desired exotherm, which, in the following tables is expressed as a percentage of air target. The differences between the catalyst which has a uniform dispersion of platinum and the catalyst which is surface impregnated with platinum are set forth in the following tables which graphically illustrate the differences. As was hereinbefore set forth catalyst A contains a uniform impregnation of platinum while Catalyst B is surface impregnated.

TABLE 2

| LOCATION OF MAXIMUM TEMPERATURE-INCHES FROM INLET OF CATALYST BED | | |
|---|---|---|
| Hours on Stream | A | B |
| 6 | 1.75 | 1.38 |
| 12 | 1.75 | 1.50 |
| 18 | 1.75 | 1.50 |
| 24 | 1.88 | 1.50 |
| 30 | 1.88 | 1.63 |
| 42 | 1.75 | 1.50 |
| 54 | 1.75 | 1.50 |
| 66 | 1.75 | 1.63 |
| 78 | 1.88 | 1.50 |
| 90 | 2.25 | 1.50 |

TABLE 3

| STYRENE COMBUSTION SELECTIVITY | | |
|---|---|---|
| Hours on Stream | A | B |
| 6 | 9.51 | 6.14 |
| 12 | 6.98 | 4.76 |
| 18 | 7.40 | 4.64 |
| 24 | 7.44 | 4.76 |
| 30 | 7.96 | 4.70 |
| 42 | 7.83 | 4.70 |
| 54 | 8.50 | 4.84 |
| 66 | 8.66 | 4.81 |
| 78 | 8.84 | 4.95 |
| 90 | 8.74 | 4.81 |

TABLE 4

| PERCENT OF AIR TARGET | | |
|---|---|---|
| Hours on Stream | A | B |
| 6 | 92.6 | 88.2 |
| 12 | 96.2 | 91.2 |
| 18 | 92.5 | 93.7 |
| 24 | 94.6 | 91.2 |
| 30 | 93.5 | 92.8 |
| 42 | 94.8 | 93.0 |
| 54 | 95.4 | 94.1 |
| 66 | 95.7 | 93.1 |
| 78 | 94.7 | 93.6 |
| 90 | 98.0 | 94.2 |

It is readily apparent from the comparisons set forth in the above tables that the surface impregnated Catalyst B of the present invention showed greater activity inasmuch as the maximum temperature of the catalyst bed was maintained in a position closer to the inlet of the bed, thus indicating the higher activity of the catalyst; the styrene combustion selectivity was lower indicating that selectivity for the desired oxidation of hydrogen is higher, while the amount of air necessary to achieve the desired exotherm was less than that which was required for the uniformly impregnated catalyst, also indicating higher activity. Surface-impregnated Catalyst B clearly shows higher stability as compared to Catalyst A as shown by the stability of the maximum temperature in the catalyst bed for Catalyst B.

EXAMPLE IV

To further illustrate the superior stability and activity of selective oxidation catalysts prepared according to the method of this invention, two additional catalysts were prepared. A conventional uniformly impregnated catalyst was prepared by peptizing a Boehmite alumina powder which had an apparent bulk density of 0.36 g/ml, with a nitric acid solution and a sufficient amount of tin tetrachloride pentahydrate to afford 0.25% of tin based on the calcined support. The mixture of nitric acid and tin tetrachloride pentahydrate was stirred at room temperature until homogeneous and added to the Boehmite powder. The mixture was stirred for a period of 6 minutes and thereafter the resultant dough was extruded, dried and calcined under similar conditions set forth in Example I above.

The calcined support was then impregnated in a rotary evaporator with solutions of chloroplatinic acid sufficient to afford 0.4 weight percent platinum, lithium nitrate in an amount sufficient to afford 0.2 weight percent lithium, and deionized water. As in the above examples, the evaporator was purged with nitrogen and the mixture cold rolled for a period of 15 minutes. At the end of this time steam was charged to the evaporator jacket and the aqueous portion of the solution was evaporated. The impregnated support was then dried and calcined again in a manner similar to that set forth in the above examples. This catalyst was designated as Catalyst C.

EXAMPLE V

A catalyst of the present invention which contained surface impregnated platinum was prepared by peptizing an identical lot of Boehmite powder having the same density as set forth in Example IV above with a solution of tin tetrachloride pentahydrate in an amount sufficient to afford 1.0 percent tin based on the calcined support. The alumina and tin tetrachloride pentahydrate were mixed for a period of 6 minutes, extruded, dried and calcined in a manner similar to that set forth in Example I above.

To afford the surface impregnation of platinum by forming a complex, the tin containing alumina was further impregnated with a solution comprising a mixture of a chloroplatinic acid in an amount sufficient to afford 0.4 weight percent platinum, lithium nitrate in an amount sufficient to afford 0.2 weight percent lithium based on the weight of the calcined support, and a sufficient amount of thiolactic acid to afford a 1:1 molar ratio of platinum to thiolactic acid in the solution. In addition, an amount of deionized water was also present in an amount to afford an impregnating solution/calcined support ratio of 1/1 (vol/vol). As in the previous examples, the impregnation was effected in a glass jacketed rotary evaporator utilizing a process similar to that previously described. This catalyst was designated as Catalyst D.

EXAMPLE VI

Catalysts C and D were tested utilizing a procedure described in Example III above, the only critical differences being that the amount of catalyst utilized in this experiment was 15 cc as opposed to 50 cc used in the previous test and the maximum catalyst temperature was maintained at 600° C. The catalysts were utilized both fresh and after a hydrothermal ageing process in order to determine both the fresh activity and the simulated aged activity. The hydrothermal ageing employed relatively severe conditions inasmuch as the catalysts were aged for a period of 24 hours at a temperature of 800° C. in an atmosphere comprising 80 mole percent steam and 20 mole percent air. This ageing process equalled a period of over 1 year of use in a commercial unit. The results of the selective oxidation are set forth in the following tables.

TABLE 5

| | Styrene Combustion Selectivity | | | |
|---|---|---|---|---|
| | Catalyst C | | Catalyst D | |
| Hours on Stream | Fresh | Aged | Fresh | Aged |
| 3 | 9.0 | 12.8 | 6.6 | 11.0 |
| 6 | 5.8 | 11.5 | 5.8 | 10.8 |
| 9 | 4.3 | 10.5 | 5.5 | 10.4 |
| 12 | 6.0 | 10.1 | 4.7 | 9.6 |
| 15 | 5.7 | 8.8 | 5.4 | 8.8 |
| 18 | 5.5 | 9.3 | 5.4 | 8.7 |
| 21 | 5.5 | 8.7 | 5.4 | 8.5 |
| 24 | 5.6 | 6.8 | 3.5 | 8.4 |

TABLE 6

| | Oxygen Conversion, Percent | | | |
|---|---|---|---|---|
| | Catalyst C | | Catalyst D | |
| Hours on Stream | Fresh | Aged | Fresh | Aged |
| 3 | 93.0 | 66.5 | 94.5 | 79.5 |
| 6 | 91.0 | 66.5 | 93.5 | 80.5 |
| 9 | 93.5 | 64.5 | 93.5 | 79.5 |
| 12 | 91.5 | 63.5 | 91.5 | 79.0 |
| 15 | 89.0 | 66.0 | 93.5 | 78.5 |
| 18 | 90.5 | 63.5 | 93.5 | 78.5 |
| 21 | 89.5 | 65.0 | 94.5 | 78.0 |
| 24 | 89.5 | 72.5 | 90.0 | 77.5 |

The above tables clearly indicate that the surface impregnated catalyst D shows a superior performance when compared to Catalyst C which was uniformly impregnated, both as to use as a fresh catalyst and after hydrothermal ageing. The surface impregnated catalyst D shows a higher initial activity as well as a higher hydrogen oxidation selectivity which is reflected in the figures describing the lower styrene combustion selectivity. In addition, the surface impregnated catalyst of the present invention also shows a much higher activity after hydrothermal ageing, thus indicating the catalyst possesses a superior stability over the uniformly impregnated Catalyst C.

We claim as our invention:

1. In a process for the dehydrogenation of a dehydrogenatable hydrocarbon with separate and intermediate selective oxidation of hydrogen which comprises the steps of:
   (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of dehydrogenated hydrocarbons, unconverted hydrocarbons, hydrogen and steam;
   (b) removing said first-reaction dehydrogenation zone effluent stream from said first-reaction dehydrogenation zone;

(c) passing said effluent stream of step (b) to a second-reaction oxidation zone which is separate and discrete from said first-reaction dehydrogenation zone;

(d) contacting said first reaction dehydrogenation zone effluent in said second-reaction oxidation zone with an oxygen-containing gas in the presence of an oxidation catalyst consisting essentially of group VIII noble metal, a Group IVA metal and a group IA or IIA metal composited on an alumina support at oxidation conditions to selectively oxidize said hydrogen within said first-reaction zone effluent to the substantial exclusion of oxidation of said unconverted and dehydrogenated hydrocarbons, wherein said exothermic selective oxidation of said hydrogen provides additional heat and thereby raises the temperature of said unconverted and dehydrogenated hydrocarbons;

(e) withdrawing said unconverted and dehydrogenated hydrocarbons from said second-reaction oxidation zone having an increased temperature with respect to the temperature of said first-reaction dehydrogenation zone effluent;

(f) passing said second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and, (g) withdrawing and recovering said dehydrogenated hydrocarbons, the improvement of which cmmprises utilizing as said oxidation catalyst an alumina support onto which the Group VIII noble metal has been surface impregnated, said Group VIII noble metal being present in the exterior surface of said alumina support of said oxidation catalyst in an average concentration of at least 10% higher than the Group VIII noble metal average concentration present in the core of said support, said exterior surface of said alumina support possessing a depth in the range of from about 10 to about 300 microns.

2. The process as set forth in claim 1 in which said dehydrogenation and oxidation conditions include a temperature in the range of from about 500° to about 700° C. and a pressure in the range of from about 0.1 to about 10 atmospheres.

3. The process as set forth in claim 1 in which said Group VIII noble metal is present in said oxidation catalyst in an amount in the range of from about 0.01% to about 5% by weight of said catalyst.

4. The process as set forth in claim 1 in which said Group IVA metal is present is said oxidation catalyst in an amount in the range of from about 0.005% to about 5% by weight of said catalyst.

5. The process as set forth in claim 1 in which said Group IA or IIA metal is present is said oxidation catalyst in an amount in the range of from about 0.005% to about 5% by weight of said catalyst.

6. The process as set forth in claim 3 in which said Group VIII noble metal is selected from the group consisting of platinum, palladium and rhodium.

7. The process as set forth in claim 4 in which said group IVA metal is selected from the group consisting of germanium, lead and tin.

8. The process as set forth in claim 5 in which said Group IA or IIA metal is selected from the group consisting of lithium, sodium, potassium, rubidium, cesium, beryllium, magnesium, calcium, strontium and barium.

9. The process as set forth in claim 1 in which said alkaline metal of said dehydrogenation catalyst is selected from the group consisting of Groups IA and IIA of the Periodic Table.

10. The process as set forth in claim 1 further characterized in that said dehydrogenation catalyst contains an oxide or sulfide or a metal selected from the group consisting of Groups IVB, VB or VIB of the Periodic Table.

11. The process as set forth in claim 1 in which said oxygen-containing gas is air.

12. The process as set forth in claim 1 in which said oxygen-containing gas is a mixture of oxygen and steam.

13. The process as set forth in claim 1 in which said dehydrogenatable hydrocarbon is ethylbenzene and said dehydrogenated hydrocarbon is styrene.

14. The process as set forth in claim 1 in which said dehydrogenatable hydrocarbon is p-diethylbenzene and said dehydrogenated hydrocarbon is p-divinylbenzene.

15. The process as set forth in claim 1 in which said dehydrogenatable hydrocarbon is o-diethylbenzene and said dehydrogenated hydrocarbon is o-divinylbenzene.

16. The process as set forth in claim 1 in which said dehydrogenatable hydrocarbon is m-diethylbenzene and said dehydrogenated hydrocarbon is m-divinylbenzene.

17. The process as set forth in claim 1 in which said dehydrogenatable hydrocarbon is p-ethyltoluene and said dehydrogenated hydrocarbon is p-methylstyrene.

* * * * *